United States Patent [19]
Lockhart et al.

[11] Patent Number: 5,556,752
[45] Date of Patent: Sep. 17, 1996

[54] SURFACE-BOUND, UNIMOLECULAR, DOUBLE-STRANDED DNA

[75] Inventors: David J. Lockhart, Santa Clara, Calif.; Dirk Vetter, Freiburg, Germany; Martin Diggelmann, Niederdorf, Switzerland

[73] Assignee: Affymetrix, Inc., Santa Clara, Calif.

[21] Appl. No.: 327,687

[22] Filed: Oct. 24, 1994

[51] Int. Cl.$^6$ ............................... C12Q 1/68; C07H 21/00
[52] U.S. Cl. ................................................. 435/6; 536/23.1
[58] Field of Search ............................. 435/6; 536/23.1; 530/413

[56] References Cited

U.S. PATENT DOCUMENTS

| | | | |
|---|---|---|---|
| 4,376,110 | 3/1983 | David et al. | 435/5 |
| 4,562,157 | 12/1985 | Lowe et al. | 435/287.2 |
| 4,728,502 | 3/1988 | Hamill | 422/116 |
| 5,143,854 | 9/1992 | Pirrung et al. | 436/518 |
| 5,288,514 | 2/1994 | Ellman | 165/155 |

FOREIGN PATENT DOCUMENTS

| | | |
|---|---|---|
| WO89/10977 | 11/1989 | WIPO . |
| WO89/11548 | 11/1989 | WIPO . |
| WO90/00626 | 1/1990 | WIPO . |
| WO90/15070 | 12/1990 | WIPO . |
| WO92/00091 | 1/1992 | WIPO . |

OTHER PUBLICATIONS

Duncan, C. H. etal (1988) Analytical Biochemistry 169: 104–108. "Affinity Chromatography of a Sequence–specific DNA binding protein using Teflon linked . . . ".

Ma, M. Y.–X. et al (1993) Biochemistry 32: 1751–1758. "Design & Synthesis of RNA Miniduplicates via a synthetic linker approach."Markiewicz, W T et al (1989) Nucleic Acids Research 17: 7149–7157. "Universal solid supports for the synthesis of oligonucleotides with 3'– $PO_4$s".

Ohlmeyer, M H J et al (1993) Proc. Natl. Acad. Sci. USA 90: 10922–10926 "Complex Synthetic Chemical Libraries Indexed with molecular Tags."Geysen, et al., *J. Immun. Meth.* 102:259–274 (1987).

Frank and Doring, *Tetrahedron*, 44:6031–6040 (1988).
Fodor et al., *Science*, 251:767–777 (1991).
Lam et al., *Nature*, 354:82–84 (1991).
Houghten et al., *Nature*, 354:84–86 (1991).
Galas et al., *Nucleic Acid Res.* 5(9):3157–3170 (1978).
Murphy et al., *Science* 262:1025–1029 (1993).
Lysov et al., *Dokl. Akad. Nauk SSSR*, 303:1508–1511 (1988) (See footnote provided, P. 436).
Bains et al., *J. Theor. Biol.*, 135:303–307 (1988).
Drmanac et al., *Genomics*, 4:114–128 (1989).
Strezoska et al., *Proc. Natl. Acad. Sci. USA*, 88:10089–10093 (1991).
Drmanac et al., *Science*, 260:1649–1652 (1993).
Needels, et al., *Proc. Natl. Acad. Sci., USA*, 90:10700–10704 (1993).
Scaria, P. V., et al. *J. of Biol. Chem.*, 266(9) : 5417–5423 (1993).

(List continued on next page.)

*Primary Examiner*—Mindy Fleisher
*Assistant Examiner*—Scott David Priebe
*Attorney, Agent, or Firm*—Townsend and Townsend and Crew LLP

[57] ABSTRACT

Libraries of unimolecular, double-stranded oligonucleotides on a solid support. These libraries are useful in pharmaceutical discovery for the screening of numerous biological samples for specific interactions between the double-stranded oligonucleotides, and peptides, proteins, drugs and RNA. In a related aspect, the present invention provides libraries of conformationally restricted probes on a solid support. The probes are restricted in their movement and flexibility using double-stranded oligonucleotides as scaffolding. The probes are also useful in various screening procedures associated with drug discovery and diagnosis. The present invention further provides methods for the preparation and screening of the above libraries.

6 Claims, 1 Drawing Sheet

OTHER PUBLICATIONS

Durand, M., et al., *Nucleic Acid Res.,* 18(21) : 6353–5469 (1990).

Famulok, M., et al., *Angew. Chem. Int. Ed. Engl.,* 31:979–988 (1992).

Chattopadhyaya, R., et al., *Nature,* 334:175–179 (1988).

Bock, L. C., et al., *Nature,* 355:564–566 (1992).

Parham, Peter, *Nature,* 360:300–301 (1992).

Tuerk, C., et al., *Science,* 249:505–510 (1990).

Mergny, J.-L., et al., *Nucleic Acids Res.,* 19(7) : 1521–1526 (1991).

Brossalina, E., et al., *J. Am. Chem. Soc.,* 115:796–797 (1993).

Härd, T., et al., *Biochemistry,* 29:959–965 (1990).

Cook, J., et al., *Analytical Biochemistry,* 190:331–339 (1990).

Cuniberti, C. et al., *Biophysical Chemistry,* 38:11–22 (1990).

Berman, H. M., et al., *Ann. Rev. Biophys. Bioeng.,* 10:87–114 (1981).

White et al. "Principles of Biochemistry" New York: McGraw–Hill, 1978 pp. 124–128.

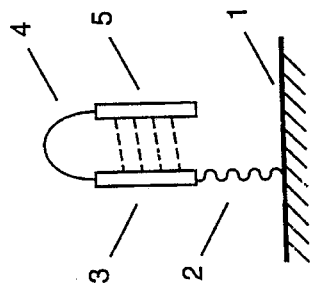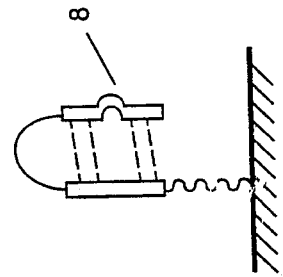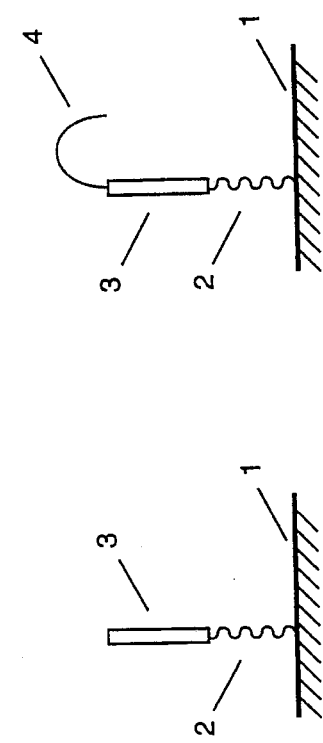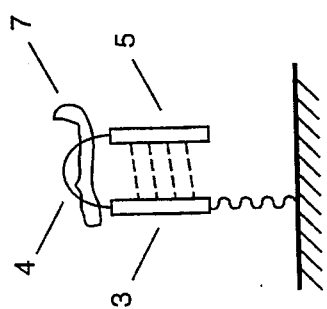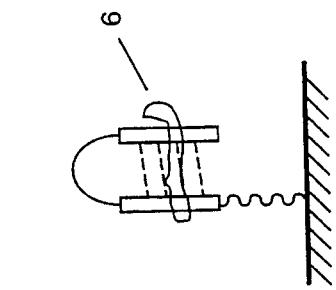
Figure 1a-1f

SURFACE-BOUND, UNIMOLECULAR, DOUBLE-STRANDED DNA

GOVERNMENT RIGHTS

Research leading to the invention was funded in part by NIH Grant No. R01HG00813-03 and the government may have certain fights to the invention.

BACKGROUND OF THE INVENTION

The present invention relates to the field of polymer synthesis and the use of polymer libraries for biological screening. More specifically, in one embodiment the invention provides arrays of diverse double-stranded oligonucleotide sequences. In another embodiment, the invention provides arrays of conformationally restricted probes, wherein the probes are held in position using double-stranded DNA sequences as scaffolding. Libraries of diverse unimolecular double-stranded nucleic acid sequences and probes may be used, for example, in screening studies for determination of binding affinity exhibited by binding proteins, drugs, or RNA.

Methods of synthesizing desired single stranded DNA sequences are well known to those of skill in the art. In particular, methods of synthesizing oligonucleotides are found in, for example, *Oligonucleotide Synthesis: A Practical Approach*, Gait, ed., IRL Press, Oxford (1984), incorporated herein by reference in its entirety for all purposes. Synthesizing unimolecular double-stranded DNA in solution has also been described. See, Durand, et al. *Nucleic Acids Res.* 18:6353–6359 (1990) and Thomson, et al. *Nucleic Acids Res.* 21:5600–5603 (1993), the disclosures of both being incorporated herein by reference.

Solid phase synthesis of biological polymers has been evolving since the early "Merrifield" solid phase peptide synthesis, described in Merrifield, *J. Am. Chem. Soc.* 85:2149–2154 (1963), incorporated herein by reference for all purposes. Solid-phase synthesis techniques have been provided for the synthesis of several peptide sequences on, for example, a number of "pins." See e.g., Geysen et al., *J. Immun. Meth.* 102:259–274 (1987), incorporated herein by reference for all purposes. Other solid-phase techniques involve, for example, synthesis of various peptide sequences on different cellulose disks supported in a column. See Frank and Doring, *Tetrahedron* 44:6031–6040 (1988), incorporated herein by reference for all purposes. Still other solid-phase techniques are described in U.S. Pat. No. 4,728,502 issued to Hamill and WO 90/00626 (Beattie, inventor).

Each of the above techniques produces only a relatively low density array of polymers. For example, the technique described in Geysen et al. is limited to producing 96 different polymers on pins spaced in the dimensions of a standard microtiter plate.

Improved methods of forming large arrays of oligonucleotides, peptides and other polymer sequences in a short period of time have been devised. Of particular note, Pirrung et al., U.S. Pat. No. 5,143,854 (see also PCT Application No. WO 90/15070) and Fodor et al., PCT Publication No. WO 92/10092, all incorporated herein by reference, disclose methods of forming vast arrays of peptides, oligonucleotides and other polymer sequences using, for example, light-directed synthesis techniques. See also, Fodor et al., *Science*, 251:767–777 (1991), also incorporated herein by reference for all purposes. These procedures are now referred to as VLSIPS™ procedures.

In the above-referenced Fodor et al., PCT application, an elegant method is described for using a computer-controlled system to direct a VLSIPS™ procedure. Using this approach, one heterogenous array of polymers is converted, through simultaneous coupling at a number of reaction sites, into a different heterogenous array. See, U.S. Pat. No. 5,384,261 and U.S. application Ser. No. 07/980,523, the disclosures of which are incorporated herein for all purposes.

The development of VLSIPS™ technology as described in the above-noted U.S. Pat. No. 5,143,854 and PCT patent publication Nos. WO 90/15070 and 92/10092, is considered pioneering technology in the fields of combinatorial synthesis and screening of combinatorial libraries. More recently, patent application Ser. No. 08/082,937, filed Jun. 25, 1993 now abandoned, describes methods for making arrays of oligonucleotide probes that can be used to check or determine a partial or complete sequence of a target nucleic acid and to detect the presence of a nucleic acid containing a specific oligonucleotide sequence.

A number of biochemical processes of pharmaceutical interest involve the interaction of some species, e.g., a drug, a peptide or protein, or RNA, with double-stranded DNA. For example, protein/DNA binding interactions are involved with a number of transcription factors as well as tumor suppression associated with the p53 protein and the genes contributing to a number of cancer conditions.

SUMMARY OF THE INVENTION

High-density arrays of diverse unimolecular, double-stranded oligonucleotides, as well as arrays of conformationally restricted probes and methods for their use are provided by virtue of the present invention. In addition, methods and devices for detecting duplex formation of oligonucleotides on an array of diverse single-stranded oligonucleotides are also provided by this invention. Further, an adhesive based on the specific binding characteristics of two arrays of complementary oligonucleotides is provided in the present invention.

According to one aspect of the present invention, libraries of unimolecular, double-stranded oligonucleotides are provided. Each member of the library is comprised of a solid support, an optional spacer for attaching the double-stranded oligonucleotide to the support and for providing sufficient space between the double-stranded oligonucleotide and the solid support for subsequent binding studies and assays, an oligonucleotide attached to the spacer and further attached to a second complementary oligonucleotide by means of a flexible linker, such that the two oligonucleotide portions exist in a double-stranded configuration. More particularly, the members of the libraries of the present invention can be represented by the formula:

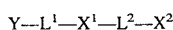

Y—L¹—X¹—L²—X² in which Y is a solid support, $L^1$ is a bond or a spacer, $L^2$ is a flexible linking group, and $X^1$ and $X^2$ are a pair of complementary oligonucleotides.

In a specific aspect of the invention, the library of different unimolecular, double-stranded oligonucleotides can be used for screening a sample for a species which binds to one or more members of the library.

In a related aspect of the invention, a library of different conformationally-restricted probes attached to a solid support is provided. The individual members each have the formula:

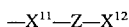

in which $X^{11}$ and $X^{12}$ are complementary oligonucleotides and Z is a probe having sufficient length such that $X^{11}$ and $X^{12}$ form a double-stranded oligonucleotide portion of the member and thereby restrict the conformations available to the probe. In a specific aspect of the invention, the library of different conformationally-restricted probes can be used for screening a sample for a species which binds to one or more probes in the library.

According to yet another aspect of the present invention, methods and devices for the bioelectronic detection of duplex formation are provided.

According to still another aspect of the invention, an adhesive is provided which comprises two surfaces of complementary oligonucleotides.

BRIEF DESCRIPTION OF THE DRAWINGS

FIGS. 1A to 1F illustrate the preparation of a member of a library of surface-bound, unimolecular double-stranded DNA as well as binding studies with receptors having specificity for either the double stranded DNA portion, a probe which is held in a conformationally restricted form by DNA scaffolding, or a bulge or loop region of RNA.

DESCRIPTION OF THE PREFERRED EMBODIMENT

Abbreviations

The following abbreviations are used herein: phi, phenanthrenequinone diimine; phen', 5-amido-glutaric acid-1,10-phenanthroline; dppz, dipyridophenazine.

Glossary

The following terms are intended to have the following general meanings as they are used herein:

Chemical terms: As used herein, the term "alkyl" refers to a saturated hydrocarbon radical which may be straight-chain or branched-chain (for example, ethyl, isopropyl, t-amyl, or 2,5-dimethylhexyl). When "alkyl" or "alkylene" is used to refer to a linking group or a spacer, it is taken to be a group having two available valences for covalent attachment, for example, $-CH_2CH_2-$, $-CH_2CH_2CH_2-$, $-CH_2CH_2CH(CH_3)CH_2-$ and $-CH_2(CH_2CH_2)_2CH_2-$. Preferred alkyl groups as substituents are those containing 1 to 10 carbon atoms, with those containing 1 to 6 carbon atoms being particularly preferred. Preferred alkyl or alkylene groups as linking groups are those containing 1 to 20 carbon atoms, with those containing 3 to 6 carbon atoms being particularly preferred. The term "polyethylene glycol" is used to refer to those molecules which have repeating units of ethylene glycol, for example, hexaethylene glycol ($HO-(CH_2CH_2O)_5-CH_2CH_2OH$). When the term "polyethylene glycol" is used to refer to linking groups and spacer groups, it would be understood by one of skill in the art that other polyethers or polyols could be used as well (i. e., polypropylene glycol or mixtures of ethylene and propylene glycols).

The term "protecting group" as used herein, refers to any of the groups which are designed to block one reactive site in a molecule while a chemical reaction is carried out at another reactive site. More particularly, the protecting groups used herein can be any of those groups described in Greene, et al., *Protective Groups In Organic Chemistry*, 2nd Ed., John Wiley & Sons, New York, N.Y, 1991, incorporated herein by reference. The proper selection of protecting groups for a particular synthesis will be governed by the overall methods employed in the synthesis. For example, in "light-directed" synthesis, discussed below, the protecting groups will be photolabile protecting groups such as NVOC, MeNPOC, and those disclosed in co-pending Application PCT/US93/10162 (filed Oct. 22, 1993), incorporated herein by reference. In other methods, protecting groups may be removed by chemical methods and include groups such as FMOC, DMT and others known to those of skill in the art.

Complementary or substantially complementary: Refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%.

Alternatively, substantial complementary exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. S. ee, M. Kanehisa *Nucleic Acids Res.* 12:203 (1984), incorporated herein by reference.

Stringent hybridization conditions will typically include salt concentrations of less than about 1M, more usually less than about 500 mM and preferably less than about 200 mM. Hybridization temperatures can be as low as 5° C., but are typically greater than 22° C., more typically greater than about 30° C., and preferably in excess of about 37° C. Longer fragments may require higher hybridization temperatures for specific hybridization. As other factors may affect the stringency. of hybridization, including base composition and length of the complementary strands, presence of organic solvents and extent of base mismatching, the combination of parameters is more important than the absolute measure of any one alone.

Epitope: The portion of an antigen molecule which is delineated by the area of interaction with the subclass of receptors known as antibodies.

Identifier tag: A means whereby one can identify which molecules have experienced a particular reaction in the synthesis of an oligomer. The identifier tag also records the step in the synthesis series in which the molecules experienced that particular monomer reaction. The identifier tag may be any recognizable feature which is, for example: microscopically distinguishable in shape, size, color, optical density, etc.; differently absorbing or emitting of light; chemically reactive; magnetically or electronically encoded; or in some other way distinctively marked with the required information. A preferred example of such an identifier tag is an oligonucleotide sequence.

Ligand/Probe: A ligand is a molecule that is recognized by a particular receptor. The agent bound by or reacting with a receptor is called a "ligand," a term which is definitionally meaningful only in terms of its counterpart receptor. The term "ligand" does not imply any particular molecular size or other structural or compositional feature other than that the substance in question is capable of binding or otherwise interacting with the receptor. Also, a ligand may serve either as the natural ligand to which the receptor binds, or as a functional analogue that may act as an agonist or antagonist.

Examples of ligands that can be investigated by this invention include, but are not restricted to, agonists and antagonists for cell membrane receptors, toxins and venoms, viral epitopes, hormones (e.g., opiates, steroids, etc.), hormone receptors, peptides, enzymes, enzyme substrates, substrate analogs, transition state analogs, cofactors, drugs, proteins, and antibodies. The term "probe" refers to those molecules which are expected to act like ligands but for which binding information is typically unknown. For example, if a receptor is known to bind a ligand which is a peptide β-turn, a "probe" or library of probes will be those molecules designed to mimic the peptide β-turn. In instances where the particular ligand associated with a given receptor is unknown, the term probe refers to those molecules designed as potential ligands for the receptor.

Monomer: Any member of the set of molecules which can be joined together to form an oligomer or polymer. The set of monomers useful in the present invention includes, but is not restricted to, for the example of oligonucleotide synthesis, the set of nucleotides consisting of adenine, thymine, cytosine, guanine, and uridine (A, T, C, G, and U, respectively) and synthetic analogs thereof. As used herein, monomers refers to any member of a basis set for synthesis of an oligomer. Different basis sets of monomers may be used at successive steps in the synthesis of a polymer.

Oligomer or Polymer: The oligomer or polymer sequences of the present invention are formed from the chemical or enzymatic addition of monomer subunits. Such oligomers include, for example, both linear, cyclic, and branched polymers of nucleic acids, polysaccharides, phospholipids, and peptides having either α-, β-, or ω-amino acids, heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which will be readily apparent to one skilled in the art upon review of this disclosure. As used herein, the term oligomer or polymer is meant to include such molecules as β-turn mimetics, prostaglandins and benzodiazepines which can also be synthesized in a stepwise fashion on a solid support.

Peptide: A peptide is an oligomer in which the monomers are amino acids and which are joined together through amide bonds and alternatively referred to as a polypeptide. In the context of this specification it should be appreciated that when α-amino acids are used, they may be the L-optical isomer or the D-optical isomer. Other amino acids which are useful in the present invention include unnatural amino acids such a β-alanine, phenylglycine, homoarginine and the like. Peptides are more than two amino acid monomers long, and often more than 20 amino acid monomers long. Standard abbreviations for amino acids are used (e.g., P for proline). These abbreviations are included in Stryer, *Biochemistry*, Third Ed., (1988), which is incorporated herein by reference for all purposes.

Oligonucleotides: An oligonucleotide is a single-stranded DNA or RNA molecule, typically prepared by synthetic means. Alternatively, naturally occurring oligonucleotides, or fragments thereof, may be isolated from their natural sources or purchased from commercial sources. Those oligonucleotides employed in the present invention will be 4 to 100 nucleotides in length, preferably from 6 to 30 nucleotides, although oligonucleotides of different length may be appropriate. Suitable oligonucleotides may be prepared by the phosphoramidite method described by Beaucage and Carruthers, *Tetrahedron Lett.*, 22:1859–1862 (1981), or by the triester method according to Matteucci, et al., *J. Am. Chem. Soc.*, 103:3185 (1981), both incorporated herein by reference, or by other chemical methods using either a commercial automated oligonucleotide synthesizer or VLSIPS™ technology (discussed in detail below). When oligonucleotides are referred to as "double-stranded," it is understood by those of skill in the art that a pair of oligonucleotides exist in a hydrogen-bonded, helical array typically associated with, for example, DNA. In addition to the 100% complementary form of double-stranded oligonucleotides, the term "double-stranded" as used herein is also meant to refer to those forms which include such structural features as bulges and loops, described more fully in such biochemistry texts as Stryer, *Biochemistry*, Third Ed., (1988), previously incorporated herein by reference for all purposes.

Receptor: A molecule that has an affinity for a given ligand or probe. Receptors may be naturally-occurring or manmade molecules. Also, they can be employed in their unaltered natural or isolated state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "ligand-receptor pair" is formed when two molecules have combined through molecular recognition to form a complex. Other examples of receptors which can be investigated by this invention include but are not restricted to:

a) Microorganism receptors: Determination of ligands or probes that bind to receptors, such as specific transport proteins or enzymes essential to survival of microorganisms, is useful in a new class of antibiotics. Of particular value would be antibiotics against opporrnistic fungi, protozoa, and those bacteria resistant to the antibiotics in current use.

b) Enzymes: For instance, the binding site of enzymes such as the enzymes responsible for cleaving neurotransmitters. Determination of ligands or probes that bind to certain receptors, and thus modulate the action of the enzymes that cleave the different neurotransmitters, is useful in the development of drugs that can be used in the treatment of disorders of neurotransmission.

c) Antibodies: For instance, the invention may be useful in investigating the ligand-binding site on the antibody molecule which combines with the epitope of an antigen of interest. Determining a sequence that mimics an antigenic epitope may lead to the development of vaccines of which the immunogen is based on one or more of such sequences, or lead to the development of related diagnostic agents or compounds useful in therapeutic treatments such as for autoimmune diseases (e.g., by blocking the binding of the "self" antibodies).

d) Nucleic Acids: The invention may be useful in investigating sequences of nucleic acids acting as binding sites for cellular proteins ("trans-acting factors"). Such sequences may include, e.g., transcription factors, suppressors, enhancers or promoter sequences.

e) Catalytic Polypeptides: Polymers, preferably polypeptides, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant. Catalytic polypeptides are described in, Lerner, R.A. et al., *Science* 252: 659 (1991), which is incorporated herein by reference.

f) Hormone receptors: For instance, the receptors for insulin and growth hormone. Determination of the ligands which bind with high affinity to a receptor is useful in the development of, for example, an oral replacement of the daily injections which diabetics must take to relieve the symptoms of diabetes, and in the other case, a replacement for the scarce human growth hormone that can only be obtained from cadavers or by recombinant DNA technology. Other examples are the vasoconstrictive hormone receptors; determination of those ligands that bind to a receptor may lead to the development of drugs to control blood pressure.

g) Opiate receptors: Determination of ligands that bind to the opiate receptors in the brain is useful in the development of less-addictive replacements for morphine and related drugs.

Substrate or Solid Support: A material having a rigid or semi-rigid surface. Such materials will preferably take the form of plates or slides, small beads, pellets, disks or other convenient forms, although other forms may be used. In some embodiments, at least one surface of the substrate will be substantially flat. In other embodiments, a roughly spherical shape is preferred.

Synthetic: Produced by in vitro chemical or enzymatic synthesis. The synthetic libraries of the present invention may be contrasted with those in viral or plasmid vectors, for instance, which may be propagated in bacterial, yeast, or other living hosts.

DESCRIPTION OF THE INVENTION

The broad concept of the present invention is illustrated in FIGS. 1A to 1F. FIGS. 1A, 1B and 1C illustrate the preparation of surface-bound unimolecular double stranded DNA, while FIGS. 1D, 1E, and 1F illustrate uses for the libraries of the present invention.

FIG. 1A shows a solid support 1 having an attached spacer 2, which is optional. Attached to the distal end of the spacer is a first oligomer 3, which can be attached as a single unit or synthesized on the support or spacer in a monomer by monomer approach. FIG. 1B shows a subsequent stage in the preparation of one member of a library according to the present invention. In this stage, a flexible linker 4 is attached to the distal end of the oligomer 3. In other embodiments, the flexible linker will be a probe. FIG. 1C shows the completed surface-bound unimolecular double stranded DNA which is one member of a library, wherein a second oligomer 5 is now attached to the distal end of the flexible linker (or probe). As shown in FIG. 1C, the length of the flexible linker (or probe) 4 is sufficient such that the first and second oligomers (which are complementary) exist in a double-stranded conformation. It will be appreciated by one of skill in the art, that the libraries of the present invention will contain multiple, individually synthesized members which can be screened for various types of activity. Three such binding events are illustrated in FIGS. 1 D, 1E and 1F.

In FIG. 1D, a receptor 6, which can be a protein, RNA molecule or other molecule which is known to bind to DNA, is introduced to the library. Determining which member of a library binds to the receptor provides information which is useful for diagnosing diseases, sequencing DNA or RNA, identifying genetic characteristics, or in drug discovery.

In FIG. 1E, the linker 4 is a probe for which binding information is sought. The probe is held in a conformationally restricted manner by the flanking oligomers 3 and 5, which are present in a double-stranded conformation. As a result, a library of conformationally restricted probes can be screened for binding activity with a receptor 7 which has specificity for the probe.

The present invention also contemplates the preparation of libraries of unimolecular, double-stranded oligonucleotides having bulges or loops in one of the strands as depicted in FIG. 1F. In FIG. 1F, one oligonucleotide 5 is shown as having a bulge 8. Specific RNA bulges are often recognized by proteins (e.g., TAR RNA is recognized by the TAT protein of HIV). Accordingly, libraries of RNA bulges or loops are useful in a number of diagnostic applications. One of skill in the art will appreciate that the bulge or loop can be present in either oligonucleotide portion 3 or 5.

Libraries of Unimolecular, Double-Stranded Oligonucleotides

In one aspect, the present invention provides libraries of unimolecular double-stranded oligonucleotides, each member of the library having the formula:

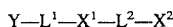

$$Y-L^1-X^1-L^2-X^2$$

in which Y represents a solid support, $X^1$ and $X^2$ represent a pair of complementary oligonucleotides, $L^1$ represents a bond or a spacer, and $L^2$ represents a linking group having sufficient length such that $X^1$ and $X^2$ form a double-stranded oligonucleotide.

The solid support may be biological, nonbiological, organic, inorganic, or a combination of any of these, existing as particles, strands, precipitates, gels, sheets, tubing, spheres, containers, capillaries, pads, slices, films, plates, slides, etc. The solid support is preferably flat but may take on alternative surface configurations. For example, the solid support may contain raised or depressed regions on which synthesis takes place. In some embodiments, the solid support will be chosen to provide appropriate light-absorbing characteristics. For example, the support may be a polymerized Langmuir Blodgett film, functionalized glass, Si, Ge, GaAs, GaP, $SiO_2$, $SiN_4$, modified silicon, or any one of a variety of gels or polymers such as (poly)tetrafluoroethylene, (poly)vinylidendifluoride, polystyrene, polycarbonate, or combinations thereof. Other suitable solid support materials will be readily apparent to those of skill in the art. Preferably, the surface of the solid support will contain reactive groups, which could be carboxyl, amino, hydroxyl, thiol, or the like. More preferably, the surface will be optically transparent and will have surface Si—OH functionalities, such as are found on silica surfaces.

Attached to the solid support is an optional spacer, $L^1$. The spacer molecules are preferably of sufficient length to permit the double-stranded oligonucleotides in the completed member of the library to interact freely with molecules exposed to the library. The spacer molecules, when present, are typically 6–50 atoms long to provide sufficient exposure for the attached double-stranded DNA molecule. The spacer, $L^1$, is comprised of a surface attaching portion and a longer chain portion. The surface attaching portion is that part of $L^1$ which is directly attached to the solid support. This portion can be attached to the solid support via carbon-carbon bonds using, for example, supports having (poly)trifluorochloroethylene surfaces, or preferably, by siloxane bonds (using, for example, glass or silicon oxide as the solid support). Siloxane bonds with the surface of the support are formed in one embodiment via reactions of surface attaching portions bearing trichlorosilyl or trialkoxysilyl groups. The surface attaching groups will also have a site for attachment of the longer chain portion. For example, groups which are suitable for attachment to a longer chain portion would include amines, hydroxyl, thiol, and carboxyl. Preferred surface attaching portions include aminoalkylsilanes and hydroxyalkylsilanes. In particularly preferred embodiments, the surface attaching portion of $L^1$ is either bis(2-hydroxyethyl)-aminopropyltriethoxysilane, 2-hydroxyethylaminopropyltriethoxysilane, aminopropyltriethoxysilane or hydroxypropyltriethoxysilane.

The longer chain portion can be any of a variety of molecules which are inert to the subsequent conditions for polymer synthesis. These longer chain portions will typically be aryl acetylene, ethylene glycol oligomers containing 2–14 monomer units, diamines, diacids, amino acids, peptides, or combinations thereof. In some embodiments, the longer chain portion is a polynucleotide. The longer chain portion which is to be used as part of $L^1$ can be selected based upon its hydrophilic/hydrophobic properties to improve presentation of the double-stranded oligonucleotides to certain receptors, proteins or drugs. The longer chain portion of $L^1$ can be constructed of polyethyleneglycols, polynucleotides, alkylene, polyalcohol, polyester, polyamine, polyphosphodiester and combinations thereof. Additionally, for use in synthesis of the libraries of the invention, $L^1$ will typically have a protecting group, attached to a functional group (i.e., hydroxyl, amino or carboxylic acid) on the distal or terminal end of the chain portion (opposite the solid support). After deprotection and coupling, the distal end is covalently bound to an oligomer.

Attached to the distal end of $L^1$ is an oligonucleotide, $X^1$, which is a single-stranded DNA or RNA molecule. The oligonucleotides which are part of the present invention are typically of from about 4 to about 100 nucleotides in length. Preferably, $X^1$ is an oligonucleotide which is about 6 to about 30 nucleotides in length. The oligonucleotide is typically linked to $L^1$ via the 3'-hydroxyl group of the oligonucleotide and a functional group on $L^1$ which results in the formation of an ether, ester, carbamate or phosphate ester linkage.

Attached to the distal end of $X^1$ is a linking group, $L^2$, which is flexible and of sufficient length that $X^1$ can effectively hybridize with $X^2$. The length of the linker will typically be a length which is at least the length spanned by two nucleotide monomers, and preferably at least four nucleotide monomers, while not be so long as to interfere with either the pairing of $X^1$ and $X^2$ or any subsequent assays. The linking group itself will typically be an alkylene group (of from about 6 to about 24 carbons in length), a polyethyleneglycol group (of from about 2 to about 24 ethyleneglycol monomers in a linear configuration), a polyalcohol group, a polyamine group (e.g., spermine, spermidine and polymeric derivatives thereof), a polyester group (e.g., poly(ethyl acrylate) having of from 3 to 15 ethyl acrylate monomers in a linear configuration), a polyphosphodiester group, or a polynucleotide (having from about 2 to about 12 nucleic acids). Preferably, the linking group will be a polyethyleneglycol group which is at least a tetraethyleneglycol, and more preferably, from about 1 to 4 hexaethyleneglycols linked in a linear array. For use in synthesis of the compounds of the invention, the linking group will be provided with functional groups which can be suitably protected or activated. The linking group will be covalently attached to each of the complementary oligonucleotides, $X^1$ and $X^2$, by means of an ether, ester, carbamate, phosphate ester or amine linkage. The flexible linking group $L^2$ will be attached to the 5'-hydroxyl of the terminal monomer of $X^1$ and to the 3'-hydroxyl of the initial monomer of $X^2$. Preferred linkages are phosphate ester linkages which can be formed in the same manner as the oligonucleotide linkages which are present in $X^1$ and $X^2$. For example, hexaethyleneglycol can be protected on one terminus with a photolabile protecting group (i.e., NVOC or MeNPOC) and activated on the other terminus with 2-cyanoethyl-N,N-diisopropylamino-chlorophosphite to form a phosphoramidite. This linking group can then be used for construction of the libraries in the same manner as the photolabile-protected, phosphoramidite-activated nucleotides. Alternatively, ester linkages to $X^1$ and $X^2$ can be formed when the $L^2$ has terminal carboxylic acid moieties (using the 5'-hydroxyl of $X^1$ and the 3'-hydroxyl of $X^2$). Other methods of forming ether, carbamate or amine linkages are known to those of skill in the art and particular reagents and references can be found in such texts as March, *Advanced Organic Chemistry*, 4th Ed., Wiley-Interscience, New York, N.Y, 1992, incorporated herein by reference.

The oligonucleotide, $X^2$, which is covalently attached to the distal end of the linking group is, like $X^1$, a single-stranded DNA or RNA molecule. The oligonucleotides which are part of the present invention are typically of from about 4 to about 100 nucleotides in length. Preferably, $X^2$ is an oligonucleotide which is about 6 to about 30 nucleotides in length and exhibits complementary to $X^1$ of from 90 to 100%. More preferably, $X^1$ and $X^2$ are 100% complementary. In one group of embodiments, either $X^1$ or $X^2$ will further comprise a bulge or loop portion and exhibit complementary of from 90 to 100% over the remainder of the oligonucleotide.

In a particularly preferred embodiment, the solid support is a silica support, the spacer is a polyethyleneglycol conjugated to an aminoalkylsilane, the linking group is a polyethyleneglycol group, and $X^1$ and $X^2$ are complementary oligonucleotides each comprising of from 6 to 30 nucleic acid monomers.

The library can have virtually any number of different members, and will be limited only by the number or variety of compounds desired to be screened in a given application and by the synthetic capabilities of the practitioner. In one group of embodiments, the library will have from 2 up to 100 members. In other groups of embodiments, the library will have between 100 and 10000 members, and between 10000 and 1000000 members, preferably on a solid support. In preferred embodiments, the library will have a density of more than 100 members at known locations per $cm^2$, preferably more than 1000 per $cm^2$, more preferably more than 10,000 per $cm^2$.

Libraries of Conformationally Restricted Probes

In still another aspect, the present invention provides libraries of conformationally-restricted probes. Each of the members of the library comprises a solid support having an optional spacer which is attached to an oligomer of the formula:

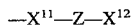

in which $X^{11}$ and $X^{12}$ are complementary oligonucleotides and Z is a probe. The probe will have sufficient length such that $X^{11}$ and $X^{12}$ form a double-stranded DNA portion of each member. $X^{11}$ and $X^{12}$ are as described above for $X^1$ and $X^2$ respectively, except that for the present aspect of the invention, each member of the probe library can have the same $X^{11}$ and the same $X^{12}$, and differ only in the probe portion. In one group of embodiments, $X^{11}$ and $X^{12}$ are either a poly-A oligonucleotide or a poly-T oligonucleotide.

As noted above, each member of the library will typically have a different probe portion. The probes, Z, can be any of a variety of structures for which receptor-probe binding information is sought for conformationally-restricted forms. For example, the probe can be an agonist or antagonist for a cell membrane receptor, a toxin, venom, vital epitope, hormone, peptide, enzyme, collector, drug, protein or antibody. In one group of embodiments, the probes are different peptides, each having of from about 4 to about 12 amino acids. Preferably the probes will be linked via polyphosphate diesters, although other linkages are also suitable. For example, the last monomer employed on the $X^{11}$ chain can be a 5'-aminopropyl-functionalized phosphoramidite nucleotide (available from Glen Research, Sterling, Va., USA or Genosys Biotechnologies, The Woodlands, Tex., USA) which will provide a synthesis initiation site for the carboxy to amino synthesis of the peptide probe. Once the peptide probe is formed, a 3'-succinylated nucleoside (from Cruachem, Sterling, Va., USA) will be added under peptide coupling conditions. In yet another group of embodiments, the probes will be oligonucleotides of from 4 to about 30 nucleic acid monomers which will form a DNA or RNA hairpin structure. For use in synthesis, the probes can also have associated functional groups (i.e., hydroxyl, amino, carboxylic acid, anhydride and derivatives thereof) for attaching two positions on the probe to each of the complementary oligonucleotides.

The surface of the solid support is preferably provided with a spacer molecule, although it will be understood that the spacer molecules are not elements of this aspect of the invention. Where present, the spacer molecules will be as described above for $L^1$.

The libraries of conformationally restricted probes can also have virtually any number of members. As above, the number of members will be limited only by design of the particular screening assay for which the library will be used, and by the synthetic capabilities of the practitioner. In one group of embodiments, the library will have from 2 to 100 members. In other groups of embodiments, the library will have between 100 and 10000 members, and between 10000 and 1000000 members. Also as above, in preferred embodiments, the library will have a density of more than 100 members at known locations per $cm^2$, preferably more than 1000 per $cm^2$, more preferably more than 10,000 per $cm^2$.

Preparation of the Libraries

The present invention further provides methods for the preparation of diverse unimolecular, double-stranded oligonucleotides on a solid support. In one group of embodiments, the surface of a solid support has a plurality of preselected regions. An oligonucleotide of from 6 to 30 monomers is formed on each of the preselected regions. A linking group is then attached to the distal end of each of the oligonucleotides. Finally, a second oligonucleotide is formed on the distal end of each linking group such that the second oligonucleotide is complementary to the oligonucleotide already present in the same preselected region. The linking group used will have sufficient length such that the complementary oligonucleotides form a unimolecular, double-stranded oligonucleotide. In another group of embodiments, each chemically distinct member of the library will be synthesized on a separate solid support.

Libraries on a Single Substrate

Light-Directed Methods

For those embodiments using a single solid support, the oligonucleotides of the present invention can be formed using a variety of techniques known to those skilled in the art of polymer synthesis on solid supports. For example, "light directed" methods (which are one technique in a family of methods known as VLSIPS™ methods) are described in U.S. Pat. No. 5,143,854, previously incorporated by reference. The light directed methods discussed in the '854 patent involve activating predefined regions of a substrate or solid support and then contacting the substrate with a preselected monomer solution. The predefined regions can be activated with a light source, typically shown through a mask (much in the manner of photolithography techniques used in integrated circuit fabrication). Other regions of the substrate remain inactive because they are blocked by the mask from illumination and remain chemically protected. Thus, a light pattern defines which regions of the substrate react with a given monomer. By repeatedly activating different sets of predefined regions and contacting different monomer solutions with the substrate, a diverse array of polymers is produced on the substrate. Of course, other steps such as washing unreacted monomer solution from the substrate can be used as necessary. Other techniques include mechanical techniques such as those described in PCT No. 92/10183, U.S. Pat. No. 5,384,261 also incorporated herein by reference for all purposes. Still further techniques include bead based techniques such as those described in PCT US/93/04145, also incorporated herein by reference, and pin based methods such as those described in U.S. Pat. No. 5,288,514, also incorporated herein by reference.

The VLSIPS™ methods are preferred for making the compounds and libraries of the present invention. The surface of a solid support, optionally modified with spacers having photolabile protecting groups such as NVOC and MeNPOC, is illuminated through a photolithographic mask, yielding reactive groups (typically hydroxyl groups) in the illuminated regions. A 3'-O-phosphoramidite activated deoxynucleoside (protected at the 5'-hydroxyl with a photolabile protecting group) is then presented to the surface and chemical coupling occurs at sites that were exposed to light. Following capping, and oxidation, the substrate is rinsed and the surface illuminated through a second mask, to expose additional hydroxyl groups for coupling. A second 5'-protected, 3'-O-phosphoramidite activated deoxynucleoside is presented to the surface. The selective photodeprotection and coupling cycles are repeated until the desired set of oligonucleotides is produced. Alternatively, an oligomer of from, for example, 4 to 30 nucleotides can be added to each of the preselected regions rather than synthesize each member in a monomer by monomer approach. At this point in the synthesis, either a flexible linking group or a probe can be attached in a similar manner. For example, a flexible linking group such as polyethylene glycol will typically having an activating group (i.e., a phosphoramidite) on one end and a photolabile protecting group attached to the other end. Suitably derivatized polyethylene glycol linking groups can be prepared by the methods described in Durand, et al. *Nucleic Acids Res.* 18:6353–6359 (1990). Briefly, a polyethylene glycol (i.e., hexaethylene glycol) can be monoprotected using MeNPOC-chloride. Following purification of the mono-protected glycol, the remaining hydroxy moiety can be activated with 2-cyanoethyl-N,N-diisopropylaminochlorophosphite. Once the flexible linking group has been attached to the first oligonucleotide ($X^1$), deprotection and coupling cycles will proceed using 5'-protected, 3'-O-phosphoramidite activated deoxynucleosides or intact oligomers. Probes can be attached in a manner similar to that used for the flexible linking group. When the desired probe is itself an oligomer, it can be formed either in stepwise fashion on the immobilized oligonucleotide or it can be separately synthesized and coupled to the immobilized oligomer in a single step. For example, preparation of conformationally restricted β-turn mimetics will typically involve synthesis of an oligonucleotide as described above, in which the last nucleoside monomer will be derivatized with an aminoalkyl-functionalized phosphoramidite. See, U.S. Pat. No. 5,288,514, previously incorporated by reference. The desired peptide probe is typically formed in the direction from carboxyl to amine terminus. Subsequent coupling of a 3'-succinylated nucleoside, for example, provides the first monomer in the construction of the complementary oligonucleotide strand (which is carried out by the above methods). Alternatively, a library of probes can be prepared by first derivatizing a solid support with multiple poly(A) or poly(T) oligonucleotides which are suitably protected with photolabile protecting groups, deprotecting at known sites and constructing the probe at those sites, then coupling the complementary poly(T) or poly(A) oligonucleotide.

Flow Channel or Spotting Methods

Additional methods applicable to library synthesis on a single substrate are described in co-pending applications Ser. No. 07/980,523, filed Nov. 20, 1992, and U.S. Pat. No. 5,384,261, incorporated herein by reference for all purposes. In the methods disclosed in these applications, reagents are delivered to the substrate by either (1) flowing within a channel defined on predefined regions or (2) "spotting" on predefined regions. However, other approaches, as well as combinations of spotting and flowing, may be employed. In each instance, certain activated regions of the substrate are mechanically separated from other regions when the monomer solutions are delivered to the various reaction sites.

A typical "flow channel" method applied to the compounds and libraries of the present invention can generally be described as follows. Diverse polymer sequences are synthesized at selected regions of a substrate or solid support by forming flow channels on a surface of the substrate through which appropriate reagents flow or in which appropriate reagents are placed. For example, assume a monomer "A" is to be bound to the substrate in a first group of selected regions. If necessary, all or part of the surface of the substrate in all or a part of the selected regions is activated for binding by, for example, flowing appropriate reagents through all or some of the channels, or by washing the entire substrate with appropriate reagents. After placement of a channel block on the surface of the substrate, a reagent having the monomer A flows through or is placed in all or some of the channel(s). The channels provide fluid contact to the first selected regions, thereby binding the monomer A on the substrate directly or indirectly (via a spacer) in the first selected regions.

Thereafter, a monomer B is coupled to second selected regions, some of which may be included among the first selected regions. The second selected regions will be in fluid contact with a second flow channel(s) through translation, rotation, or replacement of the channel block on the surface of the substrate; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the substrate at this stage of processing will be, for example, A, B, and AB. The process is repeated to form a vast array of sequences of desired length at known locations on the substrate.

After the substrate is activated, monomer A can be flowed through some of the channels, monomer B can be flowed through other channels, a monomer C can be flowed through still other channels, etc. In this manner, many or all of the reaction regions are reacted with a monomer before the channel block must be moved or the substrate must be washed and/or reactivated. By making use of many or all of the available reaction regions simultaneously, the number of washing and activation steps can be minimized.

One of skill in the art will recognize that there are alternative methods of forming channels or otherwise protecting a portion of the surface of the substrate. For example, according to some embodiments, a protective coating such as a hydrophilic or hydrophobic coating (depending upon the nature of the solvent) is utilized over portions of the substrate to be protected, sometimes in combination with materials that facilitate wetting by the reactant solution in other regions. In this manner, the flowing solutions are further prevented from passing outside of their designated flow paths.

The "spotting" methods of preparing compounds and libraries of the present invention can be implemented in much the same manner as the flow channel methods. For example, a monomer A can be delivered to and coupled with a first group of reaction regions which have been appropriately activated. Thereafter, a monomer B can be delivered to and reacted with a second group of activated reaction regions. Unlike the flow channel embodiments described above, reactants are delivered by directly depositing (rather than flowing) relatively small quantities of them in selected regions. In some steps, of course, the entire substrate surface can be sprayed or otherwise coated with a solution. In preferred embodiments, a dispenser moves from region to region, depositing only as much monomer as necessary at each stop. Typical dispensers include a micropipette to deliver the monomer solution to the substrate and a robotic system to control the position of the micropipette with respect to the substrate, or an ink-jet printer. In other embodiments, the dispenser includes a series of tubes, a manifold, an array of pipettes, or the like so that various reagents can be delivered to the reaction regions simultaneously.

Pin-Based Methods

Another method which is useful for the preparation of compounds and libraries of the present invention involves "pin based synthesis." This method is described in detail in U.S. Pat. No. 5,288,514, previously incorporated herein by reference. The method utilizes a substrate having a plurality of pins or other extensions. The pins are each inserted simultaneously into individual reagent containers in a tray. In a common embodiment, an array of 96 pins/containers is utilized.

Each tray is filled with a particular reagent for coupling in a particular chemical reaction on an individual pin. Accordingly, the trays will often contain different reagents. Since the chemistry disclosed herein has been established such that a relatively similar set of reaction conditions may be utilized to perform each of the reactions, it becomes possible to conduct multiple chemical coupling steps simultaneously. In the first step of the process the invention provides for the use of substrate(s) on which the chemical coupling steps are conducted. The substrate is optionally provided with a spacer having active sites. In the particular case of oligonucleotides, for example, the spacer may be selected from a wide variety of molecules which can be used in organic environments associated with synthesis as well as aqueous environments associated with binding studies. Examples of suitable spacers are polyethyleneglycols, dicarboxylic acids, polyamines and alkylenes, substituted with, for example, methoxy and ethoxy groups. Additionally, the spacers will have an active site on the distal end. The active sites are optionally protected initially by protecting groups. Among a wide variety of protecting groups which are useful are FMOC, BOC, t-butyl esters, t-butyl ethers, and the like. Various exemplary protecting groups are described in, for example, Atherton et al., *Solid Phase Peptide Synthesis*, IRL Press (1989), incorporated herein by reference. In some embodiments, the spacer may provide for a cleavable function by way of, for example, exposure to acid or base.

Libraries on Multiple Substrates

Bead Based Methods

Yet another method which is useful for synthesis of compounds and libraries of the present invention involves "bead based synthesis." A general approach for bead based synthesis is described copending application Ser. Nos. 07/762,522 (filed Sep. 18, 1991 now abandoned); 07/946,239 (filed Sep. 16, 1992); 08/146,886 (filed Nov. 2, 1993); 07/876,792 (filed Apr. 29, 1992) and PCT/US93/04145 (filed Apr. 28, 1993), the disclosures of which are incorporated herein by reference.

For the synthesis of molecules such as oligonucleotides on beads, a large plurality of beads are suspended in a suitable carrier (such as water) in a container. The beads are provided with optional spacer molecules having an active site. The active site is protected by an optional protecting group.

In a first step of the synthesis, the beads are divided for coupling into a plurality of containers. For the purposes of this brief description, the number of containers will be limited to three, and the monomers denoted as A, B, C, D, E, and F. The protecting groups are then removed and a first portion of the molecule to be synthesized is added to each of the three containers (i. e., A is added to container 1, B is added to container 2 and C is added to container 3).

Thereafter, the various beads are appropriately washed of excess reagents, and remixed in one container. Again, it will be recognized that by virtue of the large number of beads utilized at the outset, there will similarly be a large number of beads randomly dispersed in the container, each having a particular first portion of the monomer to be synthesized on a surface thereof.

Thereafter, the various beads are again divided for coupling in another group of three containers. The beads in the first container are deprotected and exposed to a second monomer (D), while the beads in the second and third containers are coupled to molecule portions E and F respectively. Accordingly, molecules AD, BD, and CD will be present in the first container, while AE, BE, and CE will be present in the second container, and molecules AF, BF, and CF will be present in the third container. Each bead, however, will have only a single type of molecule on its surface. Thus, all of the possible molecules formed from the first portions A, B, C, and the second portions D, E, and F have been formed.

The beads are then recombined into one container and additional steps such as are conducted to complete the synthesis of the polymer molecules. In a preferred embodiment, the beads are tagged with an identifying tag which is unique to the particular double-stranded oligonucleotide or probe which is present on each bead. A complete description of identifier tags for use in synthetic libraries is provided in co-pending application Ser. No. 08/146,886 (filed Nov. 2, 1993) previously incorporated by reference for all purposes.

Methods of Library Screening

A library prepared according to any of the methods described above can be used to screen for receptors having high affinity for either unimolecular, double-stranded oligonucleotides or conformationally restricted probes. In one group of embodiments, a solution containing a marked (labelled) receptor is introduced to the library and incubated for a suitable period of time. The library is then washed free of unbound receptor and the probes or double-stranded oligonucleotides having high affinity for the receptor are identified by identifying those regions on the surface of the library where markers are located. Suitable markers include, but are not limited to, radiolabels, chromophores, fluorophores, chemiluminescent moieties, and transition metals. Alternatively, the presence of receptors may be detected using a variety of other techniques, such as an assay with a labelled enzyme, antibody, and the like. Other techniques using various marker systems for detecting bound receptor will be readily apparent to those skilled in the art.

In a preferred embodiment, a library prepared on a single solid support (using, for example, the VLSIPS™ technique) can be exposed to a solution containing marked receptor such as a marked antibody. The receptor can be marked in any of a variety of ways, but in one embodiment marking is effected with a radioactive label. The marked antibody binds with high affinity to an immobilized antigen previously localized on the surface. After washing the surface free of unbound receptor, the surface is placed proximate to x-ray film or phosphorimagers to identify the antigens that are recognized by the antibody. Alternatively, a fluorescent marker may be provided and detection may be by way of a charge-coupled device (CCD), fluorescence microscopy or laser scanning.

When autoradiography is the detection method used, the marker is a radioactive label, such as $^{32}P$. The marker on the surface is exposed to X-ray film or a phosphorimager, which is developed and read out on a scanner. An exposure time of about 1 hour is typical in one embodiment. Fluorescence detection using a fluorophore label, such as fluorescein, attached to the receptor will usually require shorter exposure times.

Quantitative assays for receptor concentrations can also be performed according to the present invention. In a direct assay method, the surface containing localized probes prepared as described above, is incubated with a solution containing a marked receptor for a suitable period of time. The surface is then washed free of unbound receptor. The amount of marker present at predefined regions of the surface is then measured and can be related to the amount of receptor in solution. Methods and conditions for performing such assays are well-known and are presented in, for example, L. Hood et al., *Immunology*, Benjamin/Cummings (1978), and E. Harlow et al., *Antibodies. A Laboratory Manual*, Cold Spring Harbor Laboratory, (1988). See, also U.S. Pat. No. 4,376,110 for methods of performing sandwich assays. The precise conditions for performing these steps will be apparent to one skilled in the art.

A competitive assay method for two receptors can also be employed using the present invention. Methods of conducting competitive assays are known to those of skill in the art. One such method involves immobilizing conformationally restricted probes on predefined regions of a surface as described above. An unmarked first receptor is then bound to the probes on the surface having a known specific binding affinity for the receptors. A solution containing a marked second receptor is then introduced to the surface and incubated for a suitable time. The surface is then washed free of unbound reagents and the amount of marker remaining on the surface is measured. In another form of competition assay, marked and unmarked receptors can be exposed to the surface simultaneously. The amount of marker remaining on predefined regions of the surface can be related to the amount of unknown receptor in solution. Yet another form of competition assay will utilize two receptors having different labels, for example, two different chromophores.

In other embodiments, in order to detect receptor binding, the double-stranded oligonucleotides which are formed with attached probes or with a flexible linking group will be treated with an intercalating dye, preferably a fluorescent dye. The library can be scanned to establish a background fluorescence. After exposure of the library to a receptor solution, the exposed library will be scanned or illuminated and examined for those areas in which fluorescence has changed. Alternatively, the receptor of interest can be labeled with a fluorescent dye by methods known to those of skill in the art and incubated with the library of probes. The library can then be scanned or illuminated, as above, and examined for areas of fluorescence.

In instances where the libraries are synthesized on beads in a number of containers, the beads are exposed to a receptor of interest. In a preferred embodiment the receptor is fluorescently or radioactively labelled. Thereafter, one or more beads are identified that exhibit significant levels of, for example, fluorescence using one of a variety of techniques. For example, in one embodiment, mechanical separation under a microscope is utilized. The identity of the molecule on the surface of such separated beads is then identified using, for example, NMR, mass spectrometry, PCR amplification and sequencing of the associated DNA, or the like. In another embodiment, automated sorting (i.e., fluorescence activated cell sorting) can be used to separate beads (bearing probes) which bind to receptors from those which do not bind. Typically the beads will be labeled and identified by methods disclosed in Needels, et al., *Proc. Natl. Acad. Sci., USA* 90:10700–10704 (1993), incorporated herein by reference.

The assay methods described above for the libraries of the present invention will have tremendous application in such endeavors as DNA "footprinting" of proteins which bind DNA. Currently, DNA footprinting is conducted using DNase I digestion of double-stranded DNA in the presence of a putative DNA binding protein. Gel analysis of cut and protected DNA fragments then provides a "footprint" of where the protein contacts the DNA. This method is both labor and time intensive. See, Galas et al., *Nucleic Acid Res.* 5:3157 (1978). Using the above methods, a "footprint" could be produced using a single array of unimolecular, double-stranded oligonucleotides in a fraction of the time of conventional methods. Typically, the protein will be labeled with a radioactive or fluorescent species and incubated with a library of unimolecular, double-stranded DNA. Phosphorimaging or fluorescence detection will provide a footprint of those regions on the library where the protein has bound. Alternatively, unlabeled protein can be used. When unlabeled protein is used, the double-stranded oligonucleotides in the library will all be labeled with a marker, typically a fluorescent marker. Incorporation of a marker into each member of the library can be carried out by terminating the oligonucleotide synthesis with a commercially available fluorescing phosphoramidite nucleotide derivative. Following incubation with the unlabeled protein, the library will be treated with DNase I and examined for areas which are protected from cleavage.

The assay methods described above for the libraries of the present invention can also be used in reverse drug discovery. In such an application, a compound having known pharmacological safety or other desired properties (e.g., aspirin) could be screened against a variety of double-stranded oligonucleotides for potential binding. If the compound is shown to bind to a sequence associated with, for example, tumor suppression, the compound can be further examined for efficacy in the related diseases.

In other embodiments, probe arrays comprising β-turn mimetics can be prepared and assayed for activity against a particular receptor. β-turn mimetics are compounds having molecular structures similar to β-turns which are one of the three major components in protein molecular architecture. β-turns are similar in concept to hairpin turns of oligonucleotide strands, and are often critical recognition features for various protein-ligand and protein-protein interactions. As a result, a library of β-turn mimetic probes can provide or suggest new therapeutic agents having a particular affinity for a receptor which will correspond to the affinity exhibited by the β-turn and its receptor.

Bioelectronic Devices and Methods

In another aspect, the present invention provides a method for the bioelectronic detection of sequence-specific oligonucleotide hybridization. A general method and device which is useful in diagnostics in which a biochemical species is attached to the surface of a sensor is described in U.S. Pat. No. 4,562,157 (the Lowe patent), incorporated herein by reference. The present method utilizes arrays of immobilized oligonucleotides (prepared, for example, using VLSIPS™ technology) and the known photo-induced electron transfer which is mediated by a DNA double helix structure. See, Murphy et al., *Science* 262:1025–1029 (1993). This method is useful in hybridization based diagnostics, as a replacement for fluorescence-based detection systems. The method of bioelectronic detection also offers higher resolution and potentially higher sensitivity than earlier diagnostic methods involving sequencing/detecting by hybridization. As a result, this method finds applications in genetic mutation screening and primary sequencing of oligonucleotides. The method can also be used for Sequencing By Hybridization (SBH), which is described in co-pending application Ser. Nos. 08/082,937 (filed Jun. 25, 1993 now abandoned) and 08/168,904 (filed Dec. 15, 1993), each of which are incorporated herein by reference for all purposes. This method uses a set of short oligonucleotide probes of defined sequence to search for complementary sequences on a longer target strand of DNA. The hybridization pattern is used to reconstruct the target DNA sequence. Thus, the hybridization analysis of large numbers of probes can be used to sequence long stretches of DNA. In immediate applications of this hybridization methodology, a small number of probes can be used to interrogate local DNA sequence.

In the present inventive method, hybridization is monitored using bioelectronic detection. In this method, the target DNA, or first oligonucleotide, is provided with an electron-donor tag and then incubated with an array of oligonucleotide probes, each of which bears an electron-acceptor tag and. occupies a known position on the surface of the array. After hybridization of the first oligonucleotide to the array has occurred, the hybridized array is illuminated to induce an electron transfer reaction in the direction of the surface of the array. The electron transfer reaction is then detected at the location on the surface where hybridization has taken place. Typically, each of the oligonucleotide probes in an array will have an attached electron-acceptor tag located near the surface of the solid support used in preparation of the array. In embodiments in which the arrays are prepared by light-directed methods (i.e, typically 3' to 5' direction), the electronacceptor tag will be located near the 3' position. The electron-acceptor tag can be attached either to the 3' monomer by methods known to those of skill in the art, or it can be attached to a spacing group between the 3' monomer and the solid support. Such a spacing group will have, in addition to functional groups for attachment to the solid support and the oligonucleotide, a third functional group for attachment of the electronacceptor tag. The target oligonucleotide will typically have the electron-donor tag attached at the 3' position. Alternatively, the target oligonucleotide can be incubated with the array in the absence of an electron-donor tag. Following incubation, the electron-donor tag can be added in solution. The electron-donor tag will then intercalate into those regions where hybridization has occurred. An electron transfer reaction can then be detected in those regions having a continuous DNA double helix.

The electron-donor tag can be any of a variety of complexes which participate in electron transfer reactions and which can be attached to an oligonucleotide by a means which does not interfere with the electron transfer reaction. In preferred embodiments, the electron-donor tag is a ruthenium (II) complex, more preferably a ruthenium (II) (phen')$_2$(dppz) complex.

The electron-acceptor tag can be any species which, with the electron-donor tag, will participate in an electron transfer reaction. An example of an electron-acceptor tag is a rhodium (III) complex. A preferred electron-acceptor tag is a rhodium (III) (phi)$_2$(phen') complex.

In a particularly preferred embodiment, the electron-donor tag is a ruthenium (II) (phen')$_2$(dppz) complex and the electron-acceptor tag is a rhodium (III) (phi)$_2$(phen') complex.

In still another aspect, the present invention provides a device for the bioelectronic detection of sequence-specific oligonucleotide hybridization. The device will typically consist of a sensor having a surface to which an array of oligonucleotides are attached. The oligonucleotides will be attached in pre-defined areas on the surface of the sensor and have an electron-acceptor tag attached to each oligonucleotide. The electron-acceptor tag will be a tag which is capable of producing an electron transfer signal upon illumination of a hybridized species, when the complementary oligonucleotide bears an electrondonating tag. The signal will be in the direction of the sensor surface and be detected by the sensor.

In a preferred embodiment, the sensor surface will be a silicon-based surface which can sense the electronic signal induced and, if necessary, amplify the signal. The metal contacts on which the probes will be synthesized can be treated with an oxygen plasma prior to synthesis of the probes to enhance the silane adhesion and concentration on the surface. The surface will further comprise a multi-gated field effect transistor, with each gate serving as a sensor and different oligonucleotides attached to each gate. The oligonucleotides will typically be attached to the metal contacts on the sensor surface by means of a spacer group.

The spacer group should not be too long, in order to ensure that the sensing function of the device is easily activated by the binding interaction and subsequent illumination of the "tagged" hybridized oligonucleotides. Preferably, the spacer group is from 3 to 12 atoms in length and will be as described above for the surface modifying portion of the spacer group, $L^1$.

The oligonucleotides which are attached to the spacer group can be formed by any of the solid phase techniques which are known to those of skill in the art. Preferably, the oligonucleotides are formed one base at a time in the direction of the 3' terminus to the 5' terminus by the "light-directed" methods described above. The oligonucleotide can then be modified at the 3' end to attach the electron-acceptor tag. A number of suitable methods of attachment are known. For example, modification with the reagent Aminolink2 (from Applied Biosystems, Inc.) provides a terminal phosphate moiety which is derivatized with an aminohexyl phosphate ester. Coupling of a carboxylic acid, which is present on the electron-acceptor tag, to the amine can then be carried out using HOBT and DCC. Alternatively, synthesis of the oligonucleotide can begin with a suitably derivatized and protected monomer which can then be deprotected and coupled to the electron-acceptor tag once the complete oligonucleotide has been synthesized.

The silica surface can also be replaced by silicon nitride or oxynitride, or by an oxide of another metal, especially aluminum, titanium (IV) or iron (III). The surface can also be any other film, membrane, insulator or semiconductor overlying the sensor which will not interfere with the detection of electron transfer detection and to which an oligonucleotide can be coupled.

Additionally, detection devices other than an FET can be used. For example, sensors such as bipolar transistors, MOS transistors and the like are also useful for the detection of electron transfer signals.

Adhesives

In still another aspect, the present invention provides an adhesive comprising a pair of surfaces, each having a plurality of attached oligonucleotides, wherein the single-stranded oligonucleotides on one surface are complementary to the single-stranded oligonucleotides on the other surface. The strength and position/orientation specificity can be controlled using a number of factors including the number and length of oligonucleotides on each surface, the degree of complementary, and the spatial arrangement of complementary oligonucleotides on the surface. For example, increasing the number and length of the oligonucleotides on each surface will provide a stronger adhesive. Suitable lengths of oligonucleotides are typically from about 10 to about 70 nucleotides. Additionally, the surfaces of oligonucleotides can be prepared such that adhesion occurs in an extremely position-specific manner by a suitable arrangement of complementary oligonucleotides in a specific pattern. Small deviations from the optimum spatial arrangement are energetically unfavorable as many hybridization bonds must be broken and are not reformed in any other relative orientation.

The adhesives of the present invention will find use in numerous applications. Generally, the adhesives are useful for adhering two surfaces to one another. More specifically, the adhesives will find application where biological compatibility of the adhesive is desired. An example of a biological application involves use in surgical procedures where tissues must be held in fixed positions during or following the procedure. In this application, the surfaces of the adhesive will typically be membranes which are compatible with the tissues to which they are attached.

A particular advantage of the adhesives of the present invention is that when they are formed in an orientation specific manner, the adhesive portions will be "self-finding,"

that is the system will go to the thermodynamic equilibrium in which the two sides are matched in the predetermined, orientation specific manner.

EXAMPLES

Example 1

This example illustrates the general synthesis of an array of unimolecular, double-stranded oligonucleotides on a solid support.

Unimolecular double stranded DNA molecules were synthesized on a solid support using standard light-directed methods (VLSIPS™ protocols). Two hexaethylene glycol (PEG) linkers were used to covalently attach the synthesized oligonucleotides to the derivatized glass surface. Synthesis of the first (inner) strand proceeded one nucleotide at a time using repeated cycles of photo-deprotection and chemical coupling of protected nucleotides. The nucleotides each had a protecting group on the base portion of the monomer as well as a photolabile MeNPoc protecting group on the 5' hydroxyl. Upon completion of the inner strand, another MeNPoc-protected PEG linker was covalently attached to the 5' end of the surface-bound oligonucleotide. After addition of the internal PEG linker, the PEG is photodeprotected, and the synthesis of the second strand proceeded in the normal fashion. Following the synthesis cycles, the DNA bases were deprotected using standard protocols. The sequence of the second (outer) strand, being complementary to that of the inner strand, provided molecules with short, hydrogen bonded, unimolecular double-stranded structure as a result of the presence of the internal flexible PEG linker.

An array of 16 different molecules were synthesized on a derivatized glass slide in order to determine whether short, unimolecular DNA structures could be formed on a surface and whether they could adopt structures that are recognized by proteins. Each of the 16 different molecular species occupies a different physical region on the glass surface so that there is a one-to-one correspondence between molecular identity and physical location. The molecules are of the form

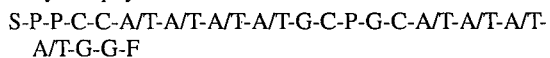
S-P-P-C-C-A/T-A/T-A/T-A/T-G-C-P-G-C-A/T-A/T-A/T-A/T-G-G-F where S is the solid surface having silyl groups, P is a PEG linker, A, C, G, and T are the DNA nucleotides, and F is a fluorescent tag. The DNA sequence is listed from the 3' to the 5' end (the 3' end of the DNA molecule is attached to the solid surface via a silyl group and 2 PEG linkers). The sixteen molecules synthesized on the solid support differed in the various permutations of A and T in the above formula.

Example 2

This example illustrates the ability of a library of surface-bound, unimolecular, double-stranded oligonucleotides to exist in duplex form and to be recognized and bound by a protein.

A library of 16 different members was prepared as described in Example 1. The 16 molecules all have the same composition (same number of As, Cs, Gs and Ts), but the order is different. Four of the molecules have an outer strand that is 100% complementary to the inner strand (these molecules will be referred to as DS, doublestranded, below). One of the four DS oligonucleotides has a sequence that is recognized by the restriction enzyme EcoR1. If the molecule can loop back and form a DNA duplex, it should be recognized and cut by the restriction enzyme, thereby releasing the fluorescent tag. Thus, the action of the enzyme provided a functional test for DNA structure, and also served to demonstrate that these structures can be recognized at the surface by proteins. The remaining 12 molecules had outer strands that were not complementary to their inner strands (referred to as SS, single-stranded, below). Of these, three had an outer strand and three had an inner strand whose sequence was an EcoR1 half-site (the sequence on one strand was correct for the enzyme, but the other half was not). The solid support with an array of molecules on the surface is referred to as a "chip" for the purposes of the following discussion. The presence of fluorescently labelled molecules on the chip was detected using confocal fluorescence microscopy. The action of various enzymes was determined by monitoring the change in the amount of fluorescence from the molecules on the chip surface (e.g. "reading" the chip) upon treatment with enzymes that can cut the DNA and release the fluorescent tag at the 5' end.

The three different enzymes used to characterize the structure of the molecules on the chip were:

1) Mung Bean Nuclease—sequence independent, single-strand specific DNA endonuclease;
2) DNase I—sequence independent, double-strand specific endonuclease;
3) EcoR1—restriction endonuclease that recognizes the sequence (5'-3')

GAATTC in double stranded DNA, and cuts between the G and the first A. Mung Bean Nuclease and EcoR1 were obtained from New England Biolabs, and DNase I was obtained from Boehringer Mannheim. All enzymes were used at a concentration of 200 units per mL in the buffer recommended by the manufacturer. The enzymatic reactions were performed in a 1 mL flow cell at 22° C., and were typically allowed to proceed for 90 minutes.

Upon treatment of the chip with the enzyme EcoR1, the fluorescence signal in the DS EcoR1 region and the 3 SS regions with the EcoR1 half-site on the outer strand was reduced by about 10% of its initial value. This reduction was at least 5 times greater than for the other regions of the chip, indicating that the action of the enzyme is sequence specific on the chip. It was not possible to determine if the factor is greater than 5 in these preliminary experiments because of uncertainty in the constancy of the fluorescence background. However, because the purpose of these early experiments was to determine whether unimolecular double-stranded structures could be formed and whether they could be specifically recognized by proteins (and not to provide a quantitative measure of enzyme specificity), qualitative differences between the different synthesis regions were sufficient.

The reduction in signal in the 3 SS regions with the EcoR1 half-site on the outer strand indicated either that the enzyme cuts single-stranded DNA with a particular sequence, or that these molecules formed a double-stranded structure that was recognized by the enzyme. The molecules on the chip surface were at a relatively high density, with an average spacing of approximately 100 angstroms. Thus, it was possible for the outer strand of one molecule to form a double-stranded structure with the outer strand of a neighboring molecule. In the case of the 3 SS regions with the EcoR1 half-site on the outer strand, such a bimolecular double-stranded region would have the correct sequence and structure to be recognized by EcoR1. However, it would differ from the unimolecular double-stranded molecules in that the inner strand remains single-stranded and thus amenable to cleavage by a single-strand specific endonuclease such as Mung Bean Nuclease. Therefore, it was possible to distinguish unimolecular from bimolecular double-stranded DNA molecules on the surface by their ability to be cut by single and double-strand specific endonucleases.

In order to remove all molecules that have single-stranded structures and to identify unimolecular double-stranded molecules, the chip was first exhaustively treated with Mung Bean Nuclease. The reduction in the fluorescence signal was greater by about a factor of 2 for the SS regions of the chip, including those with the EcoR1 half-site on the outer strand that were cleaved by EcoR1, than for the 4 DS regions. Following Mung Bean Nuclease treatment, the chip was treated with either DNase I (which cuts all remaining double-stranded molecules) or EcoR1 (which should cut only the remaining double-stranded molecules with the correct sequence). Upon treatment with DNase I, the fluorescence signal in the 4 DS regions was reduced by at least 5-fold more than the signal in the SS regions. Upon EcoR1 treatment, the signal in the single DS region with the correct EcoR1 sequence was reduced by at least a factor of 3 more than the signal in any other region on the chip. Taken together, these results indicated that the surface-bound molecules synthesized with two complementary strands separated by a flexible PEG linker form intramolecular double-stranded structures that were resistant to a single-strand specific endonuclease and were recognized by both a double-strand specific endonuclease, and a sequence-specific restriction enzyme.

What is claimed is:

1. A synthetic unimolecular, double-stranded oligonucleotide library comprising a plurality of different members, each member having the formula:

$$Y-L^1-X^1-L^2-X^2$$

wherein,

Y is a solid support;

$X^1$ and $X^2$ are a pair of complementary oligonucleotides;

$L^1$ is a spacer;

$L^2$ is a linking group having sufficient length such that $X^1$ and $X^2$ form a double-stranded oligonucleotide.

2. A library in accordance with claim 1, wherein $L^2$ is a polyethylene glycol group.

3. A library in accordance with claim 1, wherein $X^1$ and $X^2$ are complementary oligonucleotides each comprising of from 6 to 30 nucleic acid monomers.

4. A library in accordance with claim 1, wherein said solid support is a silica support and $L^1$ comprises an aminoalkylsilane and from 1 to 4 hexaethyleneglycols.

5. A library in accordance with claim 1, wherein said solid support is a silica support, $L^1$ comprises an aminoalkylsilane and from 1 to 4 hexaethyleneglycols, $L^2$ is a polyethyleneglycol group and $X^1$ and $X^2$ are complementary oligonucleotides each comprising of from 6 to 30 nucleic acid monomers.

6. A synthetic unimolecular, double-stranded oligonucleotide library of claim 1, wherein a portion of said double-stranded oligonucleotides formed by $X^1$ and $X^2$ further comprise a loop.

* * * * *